United States Patent
Cairoli (10) Patent No.: US 10,478,357 B2
(45) Date of Patent: Nov. 19, 2019

(54) BANDAGE AND MEDICAL FABRICS DISPENSERS

(71) Applicant: Rowan University, Glassboro, NJ (US)

(72) Inventor: Nicholas J. Cairoli, Newfield, NJ (US)

(73) Assignee: Rowan University, Glassboro, NJ (US)

( * ) Notice: Subject to any disclaimer, the term of this patent is extended or adjusted under 35 U.S.C. 154(b) by 488 days.

(21) Appl. No.: 15/229,294

(22) Filed: Aug. 5, 2016

(65) Prior Publication Data
US 2017/0035627 A1    Feb. 9, 2017

Related U.S. Application Data

(60) Provisional application No. 62/201,371, filed on Aug. 5, 2015.

(51) Int. Cl.
| | | |
|---|---|---|
| A61F 15/00 | (2006.01) | |
| A61F 13/02 | (2006.01) | |
| B65H 16/00 | (2006.01) | |
| B65H 37/00 | (2006.01) | |

(52) U.S. Cl.
CPC ........ *A61F 15/005* (2013.01); *A61F 13/0269* (2013.01); *A61F 15/002* (2013.01); *B65H 16/005* (2013.01); *B65H 37/005* (2013.01); *B65H 2403/41* (2013.01); *B65H 2403/542* (2013.01)

(58) Field of Classification Search
CPC .. A61F 15/005; A61F 15/002; A61F 13/0269; B65H 37/005; B65H 16/005; B65H 2403/542; B65H 2403/41
See application file for complete search history.

(56) References Cited

U.S. PATENT DOCUMENTS

| | | | | |
|---|---|---|---|---|
| 4,447,482 | A * | 5/1984 | Heinzelman | A61B 17/085 156/540 |
| 4,576,311 | A * | 3/1986 | Horton | A61L 9/12 118/235 |
| 4,718,971 | A * | 1/1988 | Summers | B65H 37/007 156/540 |
| 5,938,070 | A * | 8/1999 | Welborn | B65H 37/005 221/71 |
| 6,299,018 | B1 * | 10/2001 | Kimbrell | A61F 15/002 221/185 |
| 6,439,289 | B1 * | 8/2002 | Schlotthauer | B65C 9/0006 156/539 |

(Continued)

*Primary Examiner* — William A. Rivera
(74) *Attorney, Agent, or Firm* — Saul Ewing Arnstein & Lehr LLP; Brian R. Landry; Domingos J. Silva (57) ABSTRACT

Disclosed herein is a dispenser for adhesive fabrics or tapes, such as bandages or other adhesive medical fabrics or correction tapes. The dispenser has a case in which a supply reel and a take-up reel are mounted. A belt having adhesive fabrics or tapes thereon extends from the supply reel through one or more openings to the exterior of the case, and thence to a take-up reel. The supply reel and the take-up reel are coupled so that the belt is wrapped around the take-up reel as it is unwound from the supply reel and advances to move an adhesive fabric or tape to the exterior of the case for dispensing. The dispenser may optionally have an activation device that allows a user to extend a portion of an adhesive fabric outside the dispenser and dispense and apply the adhesive fabric to a human skin with one hand.

20 Claims, 7 Drawing Sheets

(56) References Cited

U.S. PATENT DOCUMENTS

| | | | |
|---|---|---|---|
| 7,568,580 B2* | 8/2009 | Fenton | A61F 5/08 |
| | | | 206/390 |
| 8,100,290 B2 | 1/2012 | Bizzell et al. | |
| 2008/0223511 A1* | 9/2008 | Schumacher | B65H 37/007 |
| | | | 156/230 |
| 2008/0302487 A1* | 12/2008 | Goodman | A61B 17/085 |
| | | | 156/523 |
| 2009/0218364 A1* | 9/2009 | Bizzell | A61F 15/002 |
| | | | 221/40 |
| 2009/0301663 A1* | 12/2009 | Christensen | B65H 37/007 |
| | | | 156/577 |
| 2012/0168090 A1* | 7/2012 | Kropp | B65H 37/007 |
| | | | 156/577 |
| 2013/0168025 A1* | 7/2013 | Kropp | B65H 37/007 |
| | | | 156/523 |
| 2017/0253418 A1* | 9/2017 | Roh | B65D 83/0472 |

* cited by examiner

BANDAGE AND MEDICAL FABRICS DISPENSERS

RELATED APPLICATIONS AND CLAIM OF PRIORITY

This patent document claims priority under 35 U.S.C. § 119(e) to U.S. provisional patent application No. 62/201,371, filed Aug. 5, 2015, the disclosure of which is fully incorporated herein by reference.

FIELD OF THE INVENTION

This disclosure relates to dispensers of adhesive fabrics or tapes, in particular adhesive bandages and adhesive medical fabrics.

BACKGROUND OF THE INVENTION

Adhesive medical fabrics, especially bandages, have been widely used to protect the wound from friction, bacteria, damage, or dirt for decades. Conventional adhesive bandages are typically packaged individually in a paper wrapper and placed in a box in a bundle. It is inconvenient and requires two hands to take the bandage out of the box, remove the paper wrapper and the backer paper so that the bandage may be applied. After applying the bandage, the paper wrapper and the backer paper must then be collected and discarded. The steps that are involved in applying a bandage are undesirable especially in urgent circumstances.

However, significant improvements over the conventional methods of applying bandages are still lacking, though an example of improvement has been disclosed in U.S. Pat. No. 8,100,290 (the "'290 patent"), which is incorporated herein by reference. One of the problems with adhesive bandage dispensers as disclosed in the '290 patent is that a user still needs to utilize both hands to remove the backer of a bandage and then to apply the bandage to the skin. Further, the dispenser does not collect the backer of a dispensed bandage; thus, the user must collect and discard the backer on his/her own.

This document describes devices and methods that address some or all of the issues described above.

SUMMARY OF THE INVENTION

In one embodiment, a dispenser includes a case that has a first opening extending there through, a supply reel rotatably mounted within the case and having a hub, a take-up reel rotatably mounted within the case and having a hub. The supply and the take-up reels are rotatably coupled such that the rotation of the take-up reel drives the rotation of the supply reel, or vice versa. The dispenser also includes a drive device that includes one or more gears, which can rotate at least one of the supply and the take-up reels. The supply and take-up reels can unwind or rewind a belt. The belt is capable of carrying a plurality of adhesive fabrics or tapes on a first face thereof. The belt can extend from the hub of the supply reel to a separation point at or beyond the opening and thence to the hub of the take-up reel, where each adhesive fabric can be separated from the belt as the belt advances beyond the opening from the supply reel toward the take-up reel and frictionally passes the separation point. The dispenser also includes an activation device that can extend a portion of one of the plurality of adhesive fabrics or tapes out of the opening for applying to the skin.

In one embodiment, the activation device may also include a rack and pinion gear comprising an activation button that can slide along an outside surface of the case, where the button is coupled to a rack of a rack and pinion gear and the pinion is coupled to the rack and can rotatably move relative to the rack. The pinion is also rotatably coupled to the take-up reel to drive the take-up reel.

In one embodiment, the case of the dispenser may also include a second opening and the belt can extend from the supply reel to outside the case through the first opening, thence return into the case through the second opening and thence wind onto the take-up reel.

In an alternative embodiment, a dispenser includes a case having a first opening, second opening and a third opening extending there through, a supply reel rotatably mounted within the case and having a hub, and a take-up reel rotatably mounted within the case and having a hub. The supply and the take-up reels are rotatably coupled such that rotation of the take-up reel drives rotation of the supply reel, or vice versa. The dispenser also includes a drive device that has one or more gears and can rotate at least one of the supply and the take-up reels. The supply and the take-up reels can unwind or rewind a belt. The belt may include a first strip and a second strip and capable of carrying a plurality of adhesive fabrics interposed between the first and second strips. The belt can extend from the hub of the supply reel to a separation point at or beyond the first opening and thence to the hub of the take-up reel, where each adhesive fabric can be separated from the belt as the belt advances to frictionally pass the separation point and beyond the first opening from the supply reel. The first strip may thence return to the case through the second opening and wound onto the take-up reel, and the second strip may thence return to the case through the third opening and wound onto the take-up reel.

In one embodiment, the dispenser may also include a detachable cap which covers the one or more openings on the case, the cap bearing an antiseptic material on the interior thereof.

Alternatively and/or additionally, the dispenser may also include a first compartment for holding the supply reel and the take-up wheel and a second compartment for holding the drive device.

In an embodiment, a method of dispensing a medical adhesive fabric over a wound from a dispenser described in this document using one hand may include activating the activation device to extend a portion of one of the plurality of adhesive fabrics out of the opening, holding the extended portion of the adhesive fabric against a surface of human skin proximate to a wound, applying pressure to the dispenser against the surface of the skin while moving the dispenser towards the wound such that the adhesive fabric continues to extend from the case, causing the rotation of the supply reel and the take-up reel while the belt is rewound onto the take-up reel.

In an embodiment, a roll of a belt may include a first strip, a second strip, and multiple adhesive fabrics interposed between the first and second strips. The first strip, the second strip and the plurality of adhesive fabrics can be stored in and dispensed from a dispenser, which includes a case having a first opening, a second opening and a third opening extending there through, a supply reel rotatably mounted within the case and having a hub, a take-up reel rotatably mounted within the case and having a hub. The supply reel and the take-up reel are rotatably coupled such that rotation of the take-up reel drives rotation of the supply reel, or vice versa. The case also includes a drive device that includes one or more gears and can rotate at least one of the supply reel and the take-up reel to wind or unwind a belt thereon, to extend the belt from the supply reel out of the case and to rewind a waste of the belt onto the take-up reel. The first strip, the second strip and the plurality of adhesive fabrics are capable of extending from the hub of the supply reel to a separation point of the case at or beyond the first opening, in response to the rotation of the supply reel. When the first and second strips frictionally pass through the separation point, each adhesive fabric will be separated from the first and second strips. The first and second strips will return to the case through the second and third openings, respectively and wound onto the take-up reel simultaneously, while detaching the adhesive fabric from the first strip, the second strip and the case entirely.

In one embodiment, the adhesive fabrics are bandages having two adhesive tabs and an absorbent portion interposed between the two adhesive tabs. In one embodiment, the first strip can also be an adhesive layer, and the second strip can be made of wax-coated paper, plastic, polyethylene, woven material, woven wire or woven threads, and sealed together with the first strip, by adhesion or by heat. The sealed first and second strips will contain the adhesive fabrics inside.

These and other aspects of the present invention can be better appreciated in view of the following drawings, detailed description, and claims.

DETAILED DESCRIPTION OF THE INVENTION

The disclosure relates to a dispenser for adhesive medical fabrics, such as adhesive bandages or adhesive tapes. The dispenser has the beneficial properties that it can be operated with a single hand, that it can maintain the fabric in an enclosed space prior to dispensing it, and that it can retain materials used to wrap or carry the fabric upon dispensing the fabric (rather than releasing the materials, as with many known bandage products). The dispenser can be convenient to carry, attractive, and enjoyable to operate. Operation of the dispenser can be sufficiently simple that it can be operated by individuals who do not possess medical training, such as lay persons and children.

The dispenser presents an adhesive medical fabric such as a bandage at a location and in a conformation in which an adhesive portion of the fabric can be directly applied to a surface (e.g., a skin surface at or adjacent to a wound) to adhere the fabric to the surface. In one embodiment, the entire fabric to be dispensed is available for adherence to the skin when the dispenser is applied against the surface. In another embodiment, only a portion of the fabric (e.g., only one adhesive tab of a bandage having an absorbent pad interposed between two adhesive tabs) is exposed when the dispenser is applied against the surface, and additional portions of the fabric are exposed as the dispenser is drawn across (i.e., parallel to or engaged along the face of) the surface.

The mechanisms that "carry" the bandage to the end of the roll and expose it can be the cover sheet (over top of the bandage) and the bottom nonstick sheet (underneath the bandage). These two layers sandwich the bandage being sealed into it. On the take-up reel there is an oversized gear or a series of gears that can be spun with a thumb to spin the take-up reel, which in return spins the supply reel. When the supply reel is spun it releases a bandage out of the front of the device when the two layers separate. The top layer may be nonstick, but more preferably it is something with adhesion to "pick up" the bandage so that the sticky side comes down out of the bottom of the dispenser and travels towards the front/top of dispenser.

The dispenser is now described in detail with reference to various drawings and embodiments. These drawings and examples are provided for the purpose of illustration only, and the subject matter is not limited to these drawings and embodiments, but rather encompasses all variations which are evident as a result of the teaching provided herein.

Figure 1A:
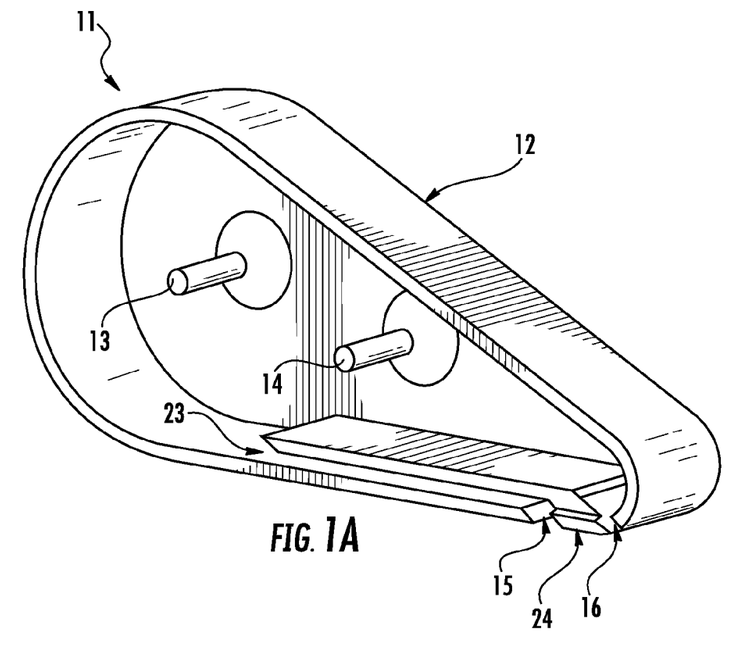
FIG. 1A illustrates a perspective view of a case according to an embodiment.
Figure 1B:
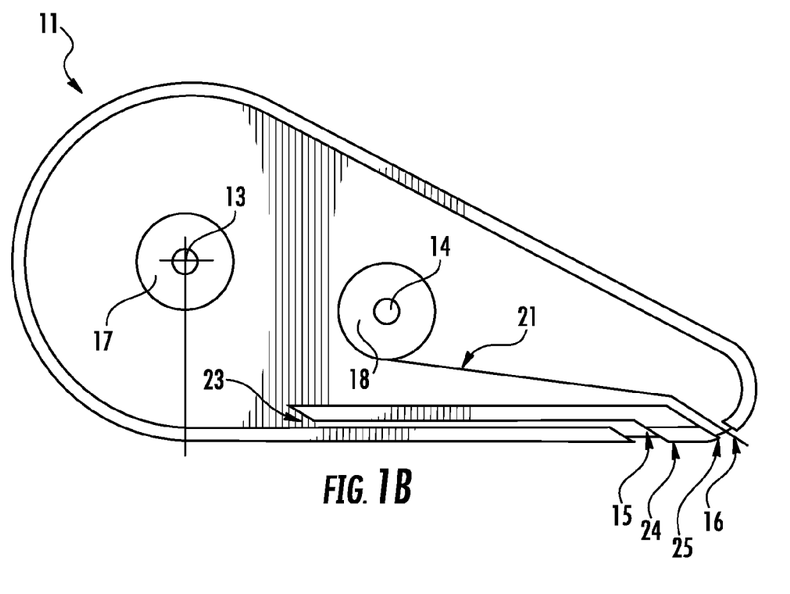
FIG. 1B illustrates a side view of a case showing interior components according to an embodiment.
Figure 1C:
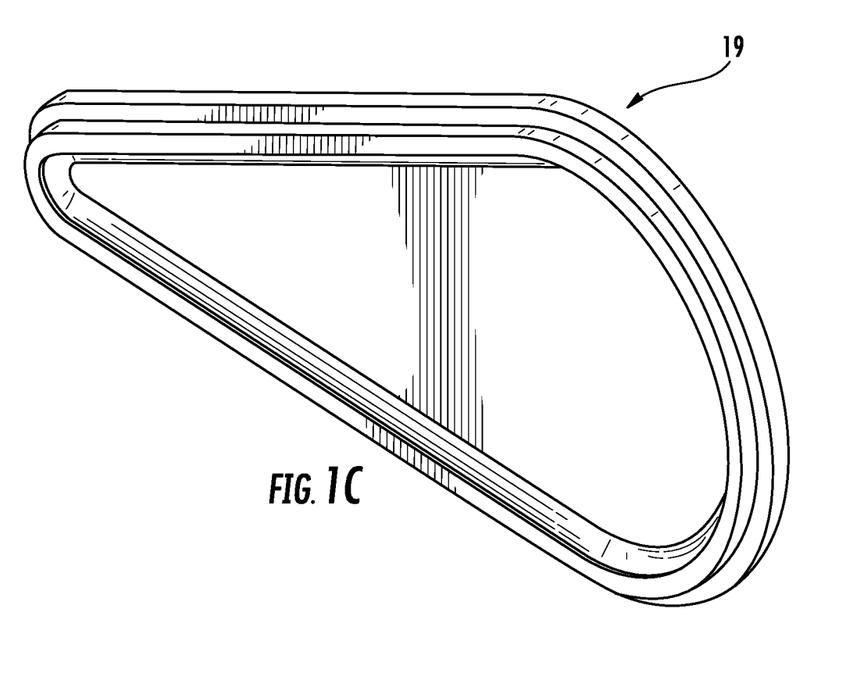
FIG. 1C illustrates a side view of the cover of the case of the embodiment shown in FIG. 1A.

With reference to FIGS. 1A, 1B and 1C, in one embodiment, the dispenser 11 has a case 12 and a cover 19. The case 12 has two sectional axles 13, 14 attached to the interior to lock a supply reel 17 and a take-up reel 18 to their respective locations. The dispenser includes a supply reel 17 and a take-up reel 18 rotatably mounted within a case. The fabric(s) to be dispensed are stored on a belt 21 that is wound about the supply reel 17. The case 12 also has one or multiple openings for guiding a belt out of the case. For example, the case 12 may have two openings 15, 16. A belt 21 has multiple bandages or medical fabrics are adhered, and may extend from the supply reel 17 through a channel 23 to a first opening 15, and then further extends through a second opening 16 to the take-up reel 18. The case may also have an exposed section 24 that is substantially flat and exposed between the first opening 15 and the second opening 16. Alternatively, the dispenser includes a case 12, a cover 19, and one opening only. Instead of exposing to the outside of the case, the belt can return and wound onto the take-up reel completely inside the case (not shown).

Returning to FIG. 1, a drive device is interposed between the supply and take-up reels and can cause the reels to turn simultaneously, so that when the belt is unwound from the supply reel 17, it is wound onto the take-up reel 18. A belt can extend from the supply reel to the take-up reel and, at least initially, carry one or more adhesive medical fabrics to be dispensed by the dispenser. The belt can extend to the exterior of the case during at least some part of its path from the supply reel to the take-up reel, so that the fabrics can be dispensed outside of the case. The case can include a pivot at which the belt is induced to change direction sharply, in order to induce detachment of fabrics from the belt at the pivot. In one embodiment, the pivot may be formed by a sharp angle 25 cross the width of the exposed section 24. When the belt returns to the take-up reel 18, the friction of the belt against the sharp angle 25 may induce detachment of fabrics from the belt. Alternatively or additionally, the pivot may be located inside the case (not shown) along the path of the belt from the supply reel to the take-up reel, and the belt can return to the take-up reel without being exposed to the outside of the case, while detaching the fabrics to outside of the case.

Figure 2A:
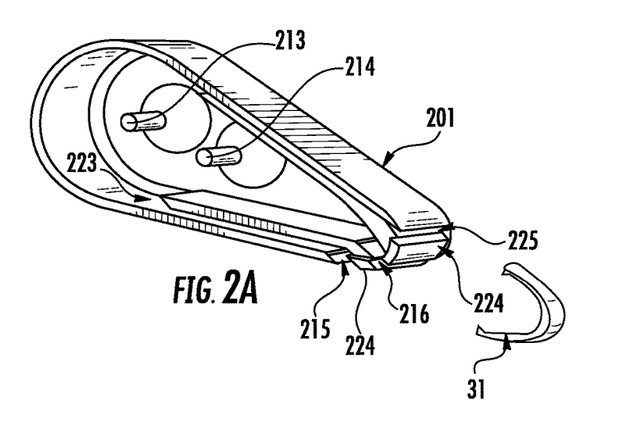
FIG. 2A illustrates a perspective view of a case according to an embodiment.
Figure 2B:
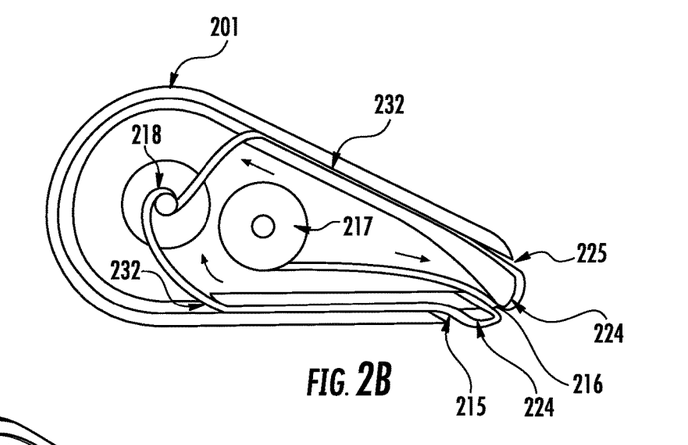
FIG. 2B illustrates a side view of a case showing interior components according to an embodiment.
Figure 2C:
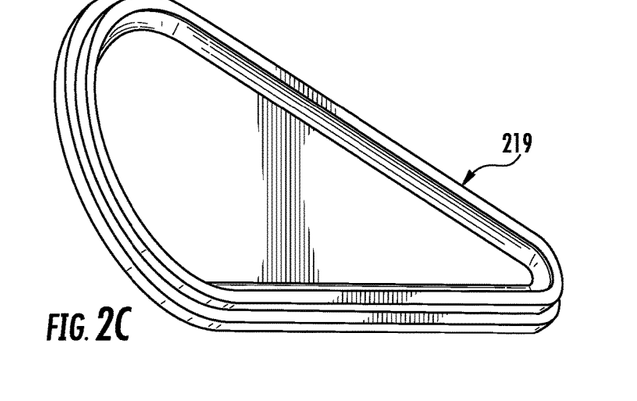
FIG. 2C illustrates a side view of the cover of the case of the embodiment shown in FIG. 2A.

With respect to FIG. 2, in an alternative embodiment, a dispenser case 201 may include two sectional axles 203, 204 attached to the interior to mount a supply reel 217 and a take-up reel 218 to their respective locations. The case 201 may have three openings 215, 216, 225, and exposed substantial flat surfaces 224 between the first and second openings 215, 216 and the second and third openings 216, 225. The flat surfaces 224 are located at the tip of the dispenser for applying the bandage to a wound, where the roll is exposed to the outside on the front of the device. The dispenser may also include a cover 219 for the case 201 and a cap 31. The operation of the three-opening case will be further explained in detail.

With reference to FIG. 2B, the supply reel 217 is rotatably mounted on the sectional axle 214 within the case and having a hub; the take-up reel 218 is also rotatably mounted on the sectional axle 213 within the case and having a hub, the supply and the take-up reels being rotatably coupled such that rotation of the take-up reel drives rotation of the supply reel, or vice versa. The belt that can utilize the embodiment may include a first strip and a second strip and capable of carrying a plurality of adhesive fabrics interposed between them. The belt 221 may extend from the hub of the supply reel 217 to a separation point at or beyond the middle opening 216 and thence to the hub of the take-up reel 218, wherein each adhesive fabric can be separated from the belt as the belt advances beyond the first opening from the supply reel and frictionally passes the separate point. The first strip thence returns to the case through the second opening 215 along the return channel/path 223 and wound onto the take-up reel 218. The second strip will also return to the case through the third opening 225 along the return channel 232 and wound onto the take-up reel 218. The case in the embodiment described in FIGS. 2A-2B may also have one or more pivots to induce detachment of the adhesive fabrics from one or more of the strips.

The case for embodiments described above preferably substantially surrounds the supply and take-up reels and at least a portion of the belt extending between the reels. By substantially surrounding these items, the case can prevent contact between contaminants (e.g., dirt or fluids) that are present in environments in which the dispenser is made, used, or stored from contacting the reels, the belt, or fabrics carried by the belt. A substantially surrounding case can thereby contribute to cleanliness or sterility of the surrounded components.

The precise construction of the case is not critical, and nor are the materials from which it is made. The case is preferably substantially rigid and preferably rotatably secures the supply and take-up reels at geometrically fixed locations relative to one another. The case can be made of plastic, metal, cardboard, or other materials, for example. Both case and cover of the case can be molded in many colors or with translucent or opaque materials. It can include a single piece, e.g., a frame bearing two axles for mounting the reels and having connected thereto a flat portion for supporting the belt between the supply and take-up reels. The materials from which the case is constructed can be transparent, translucent, or opaque. Transparent and translucent case materials have the advantage that a user can view (directly, or by holding the case interposed between his eye and a light source) the internal components, for example to assess the amount or the proportion of the belt that remains wound upon the supply reel.

The case can be composed of two or more pieces. In one embodiment, the case includes a pair of case halves of approximately the same size and approximately mirror-image construction. Each of the case halves bears a pair of hubs upon which the supply and take-up reels can be rotatably mounted. When the two case halves are connected to one another, the reels are rotatably mounted on the corresponding hubs of each of the two halves, so that the reels can rotate within the case, and the case has at least one opening to permit the belt to extend outside of the case as it is unwound from the supply reel and rewound onto the take-up reel. In another embodiment, two halves of a case carry the reels as described may define two openings between them, so that the belt can extend from the supply reel, through the first opening to the exterior of the case, thence through the second opening to return to the interior of the case and thence to the take-up reel. In this embodiment, as the belt is unwound from the supply reel, it can be extended out of the first opening to permit a bandage carried by the belt to be applied to a surface outside of the case, and the remainder of the belt can be drawn into the second opening and wound onto the take-up reel.

The case can include a cap (e.g. 31 in FIG. 2A) that covers at least a portion of the exterior of the case. The portion covered by the cap preferably includes any openings that extend through the case and any portion of the belt that is exposed on the exterior of the case when the cap is not in place. The cap can include an antiseptic or antibacterial material on its interior, so that the material is contacted against the exterior of the case (and preferably against any exposed portion of the belt) when the cap is in place.

The shape of the case is not critical, but is preferably selected to conform to the shape of the hand of a user, to facilitate use of the case to dispense the fabrics. Other preferred shape features of the case include a pivot and a flat application surface. A pivot is a portion of the case that is situated on the case and shaped so that the pivot contacts a portion of the belt that is exposed on the exterior of the case at a location at which the directions in which the belt extends are at an acute angle to one another. The pivot facilitates separation between the belt and fabrics that are attached to it; as the belt moves across the pivot, the direction in which the belt extends changes rapidly, permitting a fabric that is attached to the belt to detach therefrom as the belt traverses the pivot and changes direction, while the fabric traverses the pivot and does not substantially change the direction in which it extends.

The case preferably includes a substantially flat application surface (e.g. 14 in FIG. 1 or 214 in FIG. 2) for facilitating attachment of an adhesive fabric carried by the belt to adhere to a target surface when the flat application surface is urged against the target surface with the belt-carried fabric interposed between the target surface and the flat application surface. So long as at least some of an adhesive portion of the fabric is able to contact the target surface, the flat application surface can be used to press the adhesive portion against the target surface to induce or strengthen adherence of the fabric to the target surface.

When the case includes a flat application surface, a portion of the belt that is exposed on the exterior of the case should traverse the flat application surface, so that an adhesive fabric can be advanced to the flat application surface by advancing the belt from the supply reel to the take-up reel and thence applied to the target surface by using the flat application surface to urge the exposed portion of the belt against the target surface with the fabric interposed between them. Alternatively or additionally, the case may be turned around, and the openings coming out of the wider end of the device may create a better force to release bandages.

Returning to FIG. 1, in one embodiment, the supply reel 17 is a rotatable article which can have at least a portion of the belt wound on a hub thereof. The purpose of the supply reel is to store one or more portions of the belt upon which adhesive fabrics are carried. The stored portion of the belt is preferably stored within the interior of a substantially closed case. The belt can be simply frictionally wound around the hub or it can be fixedly attached to the hub. The materials of construction, shape, color, and size of the supply reel are not critical, so long as the reel is able to perform the functions described herein. When the case is transparent or translucent, a transparent or translucent supply reel can facilitate viewing of the amount of belt that remains wound upon the supply reel.

In one embodiment, the take-up reel 18 is to wind thereon portions of the belt that have been unwound from the supply reel and provided to a location from which an adhesive fabric carried by the belt may have been applied to a surface. Rather than leaving free belt from which one or more adhesive fabrics have been detached (i.e., resulting in a case having 'empty' belt hanging therefrom), winding the belt onto a take-up reel maintains the compactness of the dispenser and prevents tangling or snagging of the belt.

The take-up reel 18 is rotatably coupled with the supply reel 17 and is carried by (and preferably within) the case. Like the supply reel, materials of construction, shape, color, and size of the take-up reel are not critical, so long as the reel is able to perform the functions described herein. When the case is transparent or translucent, a transparent or translucent supply reel can facilitate viewing of the amount of belt that is wound upon the take-up reel.

Figure 3A:
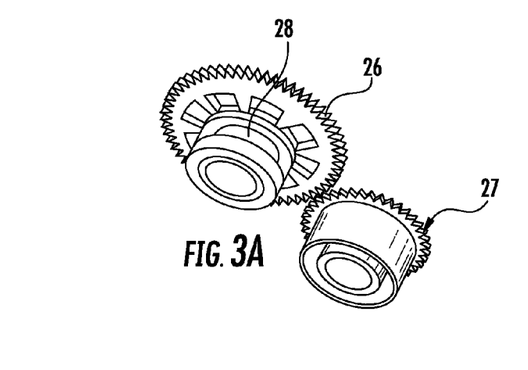
FIG. 3A illustrates a gear system of a drive device according to an embodiment.

In one embodiment, the dispenser disclosed in the embodiments described in FIG. 1 or FIG. 2 can have a drive device rotationally coupling the supply reel with the take-up reel, so that rotation of the supply reel induces a corresponding degree of rotation of the take-up reel, or vice versa. Several known devices can be used for rotationally coupling the reels. For example, with reference to FIG. 3A, a gear having teeth which engage with teeth formed on each reel is shown. The gear system may include two gears 26, 27. The gear 26 is the gear that sits on the sectional axle or pin and that the supply reel attaches to. The other gear 27 sits on the sectional axle or pin and attaches to the take-up reel. When the gear 26 turns, the take up reel will attach to the gear to force the two strands to roll. Alternatively, the roles of gears 26 and 27 may switch, i.e. the gear 26 may attach to the axle to which the take-up reel attaches and the gear 27 attaches to the supply reel. The gear system may also include a channel 28 or square to engage with a pin. For example, the case can have an indentation with an arm coming off of the gears to prevent the reels from rolling backward, as can be found on any conventional adhesive or whiteout dispensers.

Figure 3B:
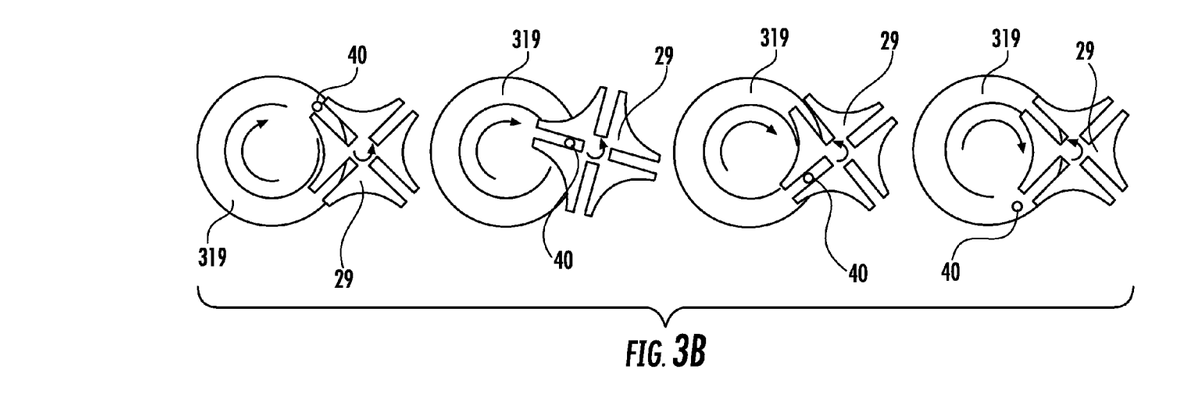
FIG. 3B illustrates a Geneva system of a drive device according to an embodiment.

With reference to FIG. 2B, a Geneva mechanism can be used as the drive device instead of gears. The Geneva mechanism comprises a drive wheel 319, a pin 40, and a driven wheel 29, wherein the drive wheel comprises a plurality of slot-containing spokes, and the pin is attached to the drive wheel and fits into the slots on the spokes, so that when the drive wheel rotates, the pin drives the driven wheel to rotate and dispense the adhesive tape. The Geneva mechanism drives the motions internally through an external switch controlled by the user through pushing, pulling, or turning.

Substantially any mechanism can be used to rotationally couple the supply and take-up reels, so long as the mechanism does not interfere with the other functions of the dispenser that are disclosed herein. For example, an elastic band that frictionally engages the hubs of both reels can be used, with frictional contact between rotating portions of the two reels.

Figure 4A:
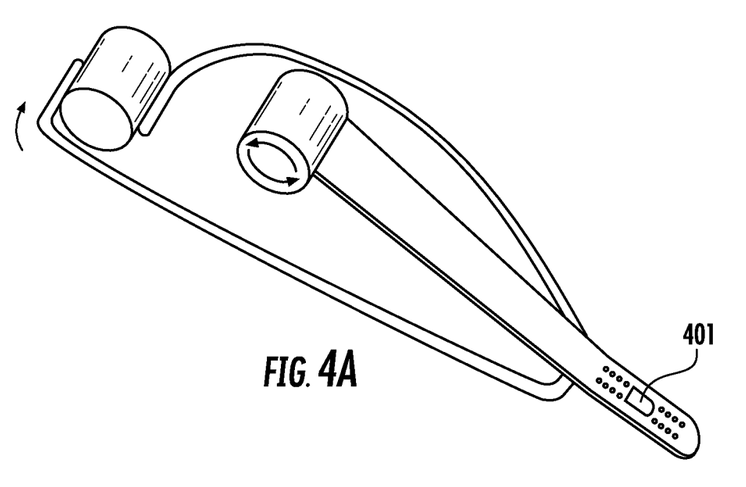
FIG. 4A illustrates a belt for bandage dispensing according to an embodiment.

With reference to FIG. 4A, the belt extends between the supply reel and the take-up reel and carries one or more adhesive fabrics 401 (e.g., bandages). The belt can be frictionally or fixedly connected with the reels, and is preferably tensioned sufficiently that winding of the belt upon the take-up reel induces unwinding of the belt from the supply reel. The tension in the belt is also sufficiently great that any portion of the belt which extends outside of the case is held taut against the exterior of the case, such as at a pivot or at a flat application surface of the case. Tension in the belt maintains the compactness of the dispenser and reduces the likelihood that the belt will become tangled or snagged upon an object other than the dispenser.

In various embodiments, one or more adhesive fabrics are carried by the belt. The way in which the adhesive fabrics are carried by the belt is not critical. The fabrics can be carried with an adhesive portion opposed against the belt. The fabrics can also be carried with an adhesive portion on a face opposite the face that is opposed against the belt. In the case of a two-or-more-piece belt, the adhesive fabrics may have a piece of the belt opposed against each of its two opposed faces.

The belt is constructed of the top and bottom layers of the supply reel proceeding to the take up reel. As stated above, the bandages will come detached when the two layers split out in the front of the device. When this split occurs, it either causes a free floating bandage (402 in FIG. 4B) or causes the bandage to stick to the top side exposing the adhesive side down and then ready to be applied to the skin. The two layers will be sealed either by adhesion or by heat to create a pocket around each bandage. The front and back sides of the bandage will be sealed. After the roll is made, it will then be sterilized through radiation.

The belt can be a continuous strip of material, such as a strip of a wax-coated paper, a strip of a plastic such as polyethylene, or a strip of a woven material, such as woven wire or woven threads. At or near its two ends, the belt is attached (frictionally or fixedly) to the hubs of the supply and take-up reels.

In one embodiment, the top layer would carry the bandage out so that the adhesive side is exposed down. Both layers will proceed to the take-up reel. The take-up reel has a square pin, and one layer will land on the front of the pin, and another layer on the back, by which the device can be made as small as possible, and both layers can be rolled up simultaneously back into one roll.

The type, construction, and identity of the adhesive fabric are not critical. In a preferred embodiment, the adhesive fabric is a conventional bandage of the sort typified by the BAND-AID brand (trademark of Johnson & Johnson) adhesive bandage strip; that is, an adhesive strip that includes an absorbent material interposed between two plastic strips bearing an adhesive. However, the adhesive fabric need not include an absorbent portion; it may also have multiple absorbent portions. The adhesive fabric may be substantially any of those known in the art, including adhesive-coated fabrics, solid plastics, perforated plastics, and the like.

The belt can include more than one strip of material. In one embodiment, one strip of material is attached to the faces of the adhesive strips that carry the adhesive and a second strip of (the same or a different) material is attached to or opposed against the opposite faces of the strips (i.e., the faces of the strips which do not bear the adhesive). The adhesive strips can be placed on the belt such that they form a substantially continuous layer (i.e., one adhesive strip ends where the next begins, separated only by a cut or gap between the strips) or they can have a substantial space between them. When the adhesive strips are spaced along the belt and a two-piece belt is used, the portions of the belt strips to which adhesive fabrics are not attached can be sealed against one another, for example to maintain cleanliness or sterility of the adhesive fabric enclosed between the belt strips. When a belt includes two or more strips of material, all strips should be attached to the take-up reel, so that all strips are wound onto the take-up reel as the dispenser is used to dispense adhesive fabrics.

The functions of the belt are to carry the adhesive fabrics prior to their dispensing, to present an adhesive strip at an appropriate location for dispensing when the belt is advanced from the supply reel, and to maintain tension in the belt as the belt is wrapped onto the take-up reel as it is advanced. In one embodiment, the dispenser may include a belt roll comprising a first strip, a second strip, and a plurality of adhesive fabrics interposed between the first and second strips. The belt roll can be configured to be stored in and dispensed from the dispenser and capable of extending from the hub of the supply reel to a separation point of the case at or beyond the first opening, in response to the rotation of the supply reel; separating each adhesive fabric from the first and second strips as the first and second strips frictionally pass through the separation point; and returning the first strip and the second strip to the case through the second opening and the third opening, respectively and wound onto the take-up reel simultaneously, while detaching the adhesive fabric from the first strip, the second strip and the case entirely.

Figure 4B:
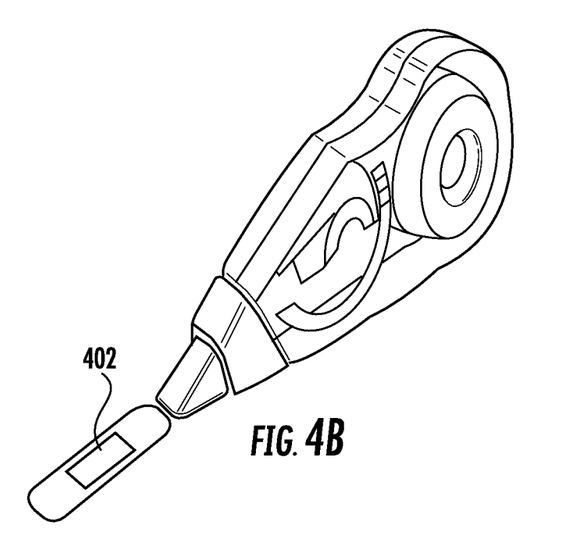
FIG. 4B illustrates a prototype of an embodiment of a bandage dispenser.
Figure 5A:
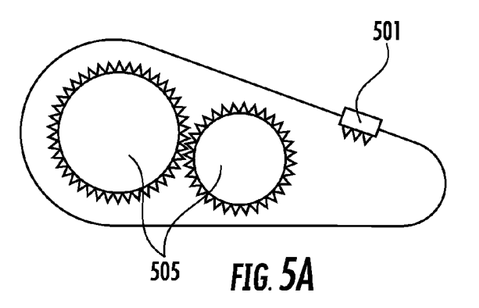
FIGS. 5A-5D illustrate a rack and pinion system of an activation device and its operation according to an embodiment.
Figure 5B:
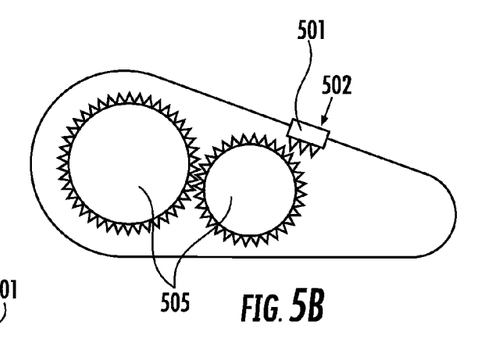
Figure 5C:
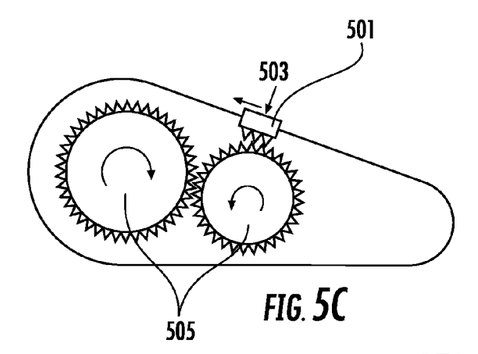
Figure 5D:
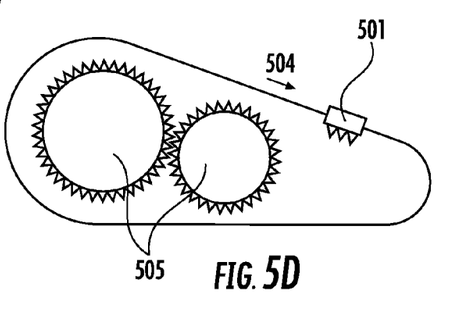

With reference to FIG. 4B, the dispenser may further include an activation device that is configured to advance the belt from the supply reel to extend at least an edge or a portion of a belt out of the case. Advance of the belt induced by the activation device causes the belt to be unwound from the supply reel to an extent that an adhesive fabric carried by the belt is carried by advancement of the belt to a flat application surface on the exterior of the case. At that location, the user is able to urge the flat application surface against a skin surface of the user (e.g., a skin surface at which a wound exists) to thereby adhere an adhesive portion of the adhesive fabric to his skin surface. If necessary, the remainder of the adhesive fabric can be exposed on the exterior of the case, either by dragging the case along the user's skin surface or by further advancing the belt using the drive mechanism until the entire of the adhesive fabric is exposed out of the case.

With reference to FIGS. 5A-5D, the activation device may use a rack and pinion gear according to an embodiment. The rack and pinion gear includes a rack coupled to an activation button 501 that can be configured to slide along an outside surface of the case, causing the rack to move linearly along the same path the button is moving. The gear also includes a pinion coupled to the rack and configured to rotatably move relative to the rack, wherein the pinion is also rotatably coupled to the supply reel to drive the supply reel or coupled to the take-up reel to drive the take-up reel. Alternatively the activation button may be itself a rack directly coupled to the rack and pinion gear. Optionally the pinion may be itself a part of the drive device, for example, a part of the gear in the embodiment described in FIG. 3A.

With further reference to FIGS. 5A-5D, the user would first push down 502 the activation button 501, which would make the rack come in contact with the gear that is coupled to or part of the drive device 505, then the user would keep pushing down and pull back 503 the activation button 501, making the rack turn the gear or drive device 505, finally the user would release the activation button/rack which would bring the button/rack up and forward, back to the resting position 504, which is over top of the gear. This would be achieved by a flexible plastic channel or two springs, one to keep pressure holding the button upward one to keep the pressure holding the button forward. When the button is in the resting state the gear and the drive device 505 can freely turn because the button/rack is not in contact with the gear. The only way it would not turn is if the user held the button down. The disclosed embodiment would allow one or both of the supply and take-up reels to be rotatable by a user without opening the case.

Alternatively, a drive mechanism (e.g., a thumb-operated gear operatively linked to turn the take-up reel or an edge of the take-up reel that can be frictionally rotated by a user) can drive rotation of the take-up reel to wind the belt thereon.

Figure 6:
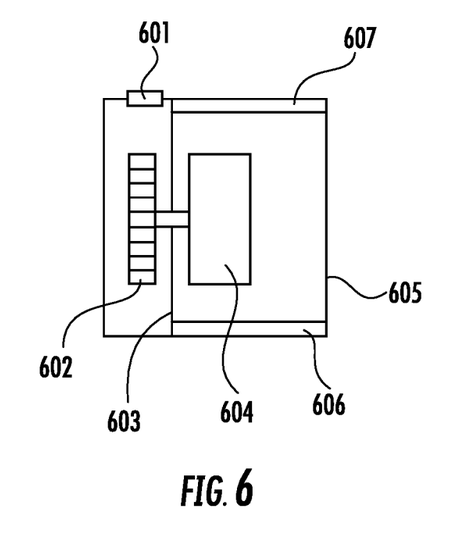
FIG. 6 illustrates an example of a two-compartment case according to an embodiment.

With reference to FIG. 6, a two-compartment structure of the case is shown. The case 605 may include two compartments divided by a middle wall 603. One side of the compartment will hold the gear or drive device 602 and attach the activation button/rack 601. The other side of the compartment will hold the supply reel and take-up reel and define the return openings and channels 606, 607 for the belt. This is where the middle wall 603 is significant because without the middle wall the activation button 601 would interfere with the return channels 606, 607 and the dispenser would not operate correctly. The button/rack would only be in the gear side of the case. There would be a hole in the middle wall and the gears would have pins connecting them to the spool reel going through the case. The hole in the case would be just big enough for the pin and it would hold the gears and spools tight.

Using the various embodiments described in FIGS. 1-6, a user of the dispenser may advance the belt sufficiently to expose at least an adhesive portion of a fabric to be dispensed. A corresponding amount of the belt is wound onto the take-up reel as the belt is unwound from the supply reel. Once at least an adhesive portion of a fabric is exposed on the exterior of the case, the adhesive portion can be adhered to a surface. The remainder of the fabric can be adhered to the surface in a number of ways. Preferably, the case is dragged across (i.e., parallel to) the surface in the direction approximately along the length of the portion of the belt that is outside the case; the belt is thereby advanced sufficiently to expose the remainder of the fabric so that it can be adhered to the surface and released from the belt. Alternatively, a drive mechanism engaged with one or both of the supply and take-up reels can be activated to unwind the belt from the supply reel and wrap it around the take-up reel, thereby advancing the belt and exposing the remainder of the fabric. As the fabric is attached to the surface, it can be detached from the belt. The precise timing of attachment to the surface and detachment from the belt is not critical. The fabric can, for example, be temporarily attached to the surface (by way of an adhesive portion of the fabric) and simultaneously attached to the belt.

An easy way to explain the operation of the dispenser is as if the user were to apply a correction tape dispenser onto a paper with one hand. The belt will consist of a top layer (e.g. adhesive tape or comparable) and a bottom layer (e.g. wax paper) sandwiching the bandage inside and sealing it from contamination. As these two layers are split apart just outside of the front of the case the bandage will then protrude out the front of the case making the sticky side face down. This action will happen when the activation button/rack is depressed and slid back, so that it causes the gears or drive device to spin allowing the rolls to spin and allowing the bandage to come out of the front of the case. The user will then touch the end of the bandage down just before a cut or scrape, or desired spot for bandage, and hover over the location (wound etc) then touch down just after it. This can all be achieved with one hand just like a user would a correction tape dispenser.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A dispenser comprising:
   a case defining a first opening extending therethrough;
   a supply reel rotatably mounted within the case and having a hub;
   a take-up reel rotatably mounted within the case and having a hub, the supply and the take-up reels being rotatably coupled such that a rotation of one of the reels drives a rotation of the other reel;
   a drive device comprising one or more gears and configured to rotate at least one of the supply and the take-up reels to unwind or rewind a belt thereon, wherein the belt is capable of carrying a plurality of adhesive fabrics or tapes on a first face thereof; and
   an activation device configured to slide along an outside surface of the case to advance a portion of one of the plurality of adhesive fabrics or tapes out of the opening;
   wherein the dispenser is configured to extend the belt from the hub of the supply reel to a separation point at or beyond the opening and thence to the hub of the take-up reel, whereby each adhesive fabric can be separated from the belt as the belt advances to frictionally pass the separation point and beyond the opening from the supply reel toward the take-up reel;
   wherein the case defines a second opening and a third opening, and the belt comprises first strip and a second strip, with the adhesive fabrics interposed there in between, wherein the dispenser is further configured to unwind the belt from the supply reel and extend through the first opening so that the first and second strips are split outside the first opening, and configured to channel back the first strip to the case through the second opening and wind the first strip onto the take-up reel and channel back second strip to the case through the third opening and wind the second strip onto the take-up reel.

2. The dispenser of claim 1, wherein the activation device comprises a rack and pinion gear comprising a rack coupled to an activation button that is configured to slide along an outside surface of the case and a pinion coupled to the rack and configured to rotatably move relative to the rack, wherein the pinion is also rotatably coupled to the supply reel or the take-up reel to drive the supply reel or the take-up reel.

3. The dispenser of claim 1, wherein the case comprises a second opening and wherein the belt is configured to extend from the supply reel to outside the case through the first opening, thence return into the case through the second opening and thence wind onto the take-up reel.

4. The dispenser of claim 1, wherein the case comprises a pivot disposed adjacent to the separation point.

5. The dispenser of claim 1, wherein the case further comprises a detachable cap which covers the first opening, the cap bearing an antiseptic material on the interior thereof.

6. The dispenser of claim 1, wherein the drive device comprises a Geneva mechanism.

7. The dispenser of claim 1, wherein the case comprises a first compartment holding the supply reel and the take-up wheel and a second compartment holding the drive device.

8. A dispenser comprising:
   a case having a first opening, second opening and a third opening extending therethrough;
   a supply reel rotatably mounted within the case and having a hub;
   a take-up reel rotatably mounted within the case and having a hub, the supply and the take-up reels being rotatably coupled such that rotation of one of the reels drives rotation of the other reel; and
   a drive device comprising one or more gears and configured to rotate at least one of the supply and the take-up reels to wind or unwind a belt thereon, wherein the belt comprises a first strip and a second strip and capable of carrying a plurality of adhesive fabrics interposed there in between;
   wherein and the dispenser is further configured to extend the belt from the hub of the supply reel to a separation point at or beyond the first opening and thence to the hub of the take-up reel, wherein each adhesive fabric can be separated from the belt as the belt advances beyond the first opening from the supply reel, and wherein the first strip thence returns to the case through the second opening and wound onto the take-up reel, and wherein the second strip thence returns to the case through the third opening and wound onto the take-up reel.

9. The dispenser of claim 8 further comprising an activation device configured to extend a portion of one of the plurality of adhesive fabrics out of the first opening.

10. The dispenser of claim 9, wherein the activation device comprises a rack and pinion gear comprising a rack coupled to an activation button that is configured to slide along an outside surface of the case and a pinion coupled to the rack and configured to rotatably move relative to the rack, wherein the pinion is also rotatably coupled to the supply reel or the take-up reel to drive the supply reel or the take-up reel.

11. The dispenser of claim 8, wherein the case comprises a pivot disposed adjacent to the separation point.

12. The dispenser of claim 8, wherein the case further comprises a detachable cap which covers the first opening, the cap bearing an antiseptic material on the interior thereof.

13. The dispenser of claim 8, wherein the drive device comprises a Geneva mechanism.

14. The dispenser of claim 8, wherein the case comprises a first compartment holding the supply reel and the take-up wheel and a second compartment holding the drive device.

15. The dispenser of claim 8 further comprising a belt roll comprising a first strip, a second strip, and a plurality of adhesive fabrics interposed between the first and second strips, wherein the first strip, the second strip and the plurality of adhesive fabrics are configured to be stored in and dispensed from the dispenser and capable of:

extending from the hub of the supply reel to a separation point of the case at or beyond the first opening, in response to the rotation of the supply reel;

separating each adhesive fabric from the first and second strips as the first and second strips frictionally pass through the separation point; and     returning the first strip and the second strip to the case through the second opening and the third opening, respectively and wound onto the take-up reel simultaneously, while detaching the adhesive fabric from the first strip, the second strip and the case entirely.

16. A method of dispensing a medical adhesive fabric over a wound from a dispenser with one hand, wherein the dispenser comprises:

a case defining a first opening extending therethrough;

a supply reel rotatably mounted within the case and having a hub;

a take-up reel rotatably mounted within the case and having a hub, the supply and the take-up reels being rotatably coupled such that rotation of one of the reels drives rotation of the other reel;

a drive device for rotating at least one of the supply and the take-up reels to wind or rewind a belt, the belt comprising a plurality of medical adhesive fabrics disposed on a first face of the belt; and     an activation device configured to extend one of the plurality of adhesive fabrics out of the opening;

wherein the case defines a second opening and a third opening, and the belt comprises first strip and a second strip, with the adhesive fabrics interposed there in between, wherein the dispenser is further configured to unwind the belt from the supply reel and extend through the first opening so that the first and second strips are split outside the first opening, and configured to channel back the first strip to the case through the second opening and wind the first strip onto the take-up reel and channel back second strip to the case through the third opening and wind the second strip onto the take-up reel;

the method comprising the steps of:

activating the activation device to extend the belt from the hub of the supply reel to extend a portion of one of the plurality of adhesive fabrics out of the opening;

holding the extended portion of the adhesive fabric against a surface of human skin proximate to a wound; and     applying pressure to the dispenser against the surface of the skin while moving the dispenser towards the wound such that the adhesive fabric continues to extend from the case, causing the rotation of the supply reel and the take-up reel while the belt is rewound onto the take-up reel;

whereby each adhesive fabric can be separated from the belt as the belt advances beyond the opening from the supply reel toward the take-up reel and frictionally passes a separation point on the case.

17. The method of claim 16, wherein activating the activation device comprises sliding an activation button along an outside surface of the case, wherein the activation button is coupled to a rack in a rack and pinion gear, wherein the pinion is coupled to the rack and configured to rotatably move relative to the rack, and wherein the pinion is also rotatably coupled to the supply reel or the take-up reel to drive the supply reel or the take-up reel.

18. A roll of a belt comprising:

a first strip;

a second strip; and a plurality of adhesive fabrics interposed between the first and second strips;

wherein the first strip, the second strip and the plurality of adhesive fabrics are configured to be stored in and dispensed from a dispenser, the dispenser comprising:

a case having a first opening, a second opening and a third opening extending therethrough,         a supply reel, rotatably mounted within the case and having a hub,         a take-up reel, rotatably mounted within the case and having a hub, the supply and the take-up reels being rotatably coupled such that rotation of the take-up reel drives rotation of the supply reel, and         a drive device comprising one or more gears and configured to rotate at least one of the supply and the take-up reels to wind or unwind a belt thereon, to extend the belt from the supply reel out of the case and to rewind a waste of the belt onto the take-up reel;

wherein the first strip, the second strip and the plurality of adhesive fabrics are capable of:

extending from the hub of the supply reel to a separation point of the case at or beyond the first opening, in response to the rotation of the supply reel,         separating each adhesive fabric from the first and second strips as the first and second strips frictionally pass through the separation point, and         returning the first strip and the second strip to the case through the second opening and the third opening, respectively and wound onto the take-up reel simultaneously, while detaching the adhesive fabric from the first strip, the second strip and the case entirely.

19. The roll of claim 18, wherein the adhesive fabrics are bandages comprising two adhesive tabs and an absorbent portion interposed between the two adhesive tabs.

20. The roll of claim 18, wherein:

the first strip is an adhesive layer;

the second strip is made of wax-coated paper, plastic, polyethylene, woven material, woven wire or woven threads; and the first strip and the second strip are sealed by adhesion or by heat containing the adhesive fabrics inside.

* * * * *